United States Patent [19]

Weeks

[11] Plant 4,708

[45] May 5, 1981

[54] ROSE PLANT

[76] Inventor: O. L. Weeks, 4759 Philadelphia St., Chino, Calif. 91710

[21] Appl. No.: 142,361

[22] Filed: Apr. 21, 1980

[51] Int. Cl.[3] ..... A01H 5/00

[52] U.S. Cl. ..... Plt./19

[58] Field of Search ..... Plt./18–19

*Primary Examiner*—Robert E. Bagwill

*Attorney, Agent, or Firm*—Vincent G. Gioia

[57] ABSTRACT

A new hybrid tea rose variety of brick red flower coloring, which darkens upon aging and a vigorously growing plant.

1 Drawing Figure

1

The present invention relates to a new and distinct variety of rose plant of the hybrid tea rose class, which was originated by my crossing as seed and pollen parents unnamed, unpatented and unreleased seedlings of my creation.

Among the novel characteristics possessed by this new variety which distinguish it from its parents and all other varieties of which I am aware are its brick red flower coloring which darkens upon aging to Jasper red, a tall, upright growing plant producing an abundance of blooms which are borne singly one to a stem. Flowers are exceptionally long lasting on the plant and as a cut flower. Asexual reproduction by budding of the new variety as performed in San Bernardino County, Calif., shows that the foregoing and other distinguishing characteristics come true to form and are established and transmitted through succeeding propagations.

The new and improved rose variety which I have developed is hybrid tea rose with singly-borne brick red blooms of hybrid-tea form displayed on a vigorous upright, free branching plant with abundant disease resistant foliage. The flowers are of good petalage and substance making them last well on the plant and as cut flowers. The attractive color darkening, with scattered light color highlights upon aging is very unusual.

The seed and pollen parents are seedlings of mine resulting from a series of crosses. The seed parent differs in flower color and growth habit from the new variety which is more vigorous and produces flowers on long straight stems. The pollen parent also differs from the new variety in plant growth habit but in flower form and color as well.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "35B" is plate 35B of the Royal Horticultural Society Color Chart.

Parentage: Seedling.

*Seed parent.*—Unnamed and unreleased seedling.

*Pollen parent.*—Unnamed and unreleased seedling.

Class: Hybrid tea.

2

The following observations are made of specimens grown outdoors in San Bernardino County, Calif., during the month of October.

FLOWER

Blooming habit: Intermittent to continuous.

A. *Bud.*—(1) Size: Medium. (2) Form: Long, pointed. (3) Color: When sepals first divide — 35B. When petals begin to unfurl — sepals fall away to reveal maize yellow 21D at point of attachment shading to brick red 35A and 35B. (4) Sepals: Simple, about same length as bud, some foliaciousness. (5) Peduncle: Length — medium with numerous tiny prickles. Aspect — straight. Strength — erect, stiff. Color — 139B.

B. *Bloom.*—(1) Size: Average size when fully expanded — about 3½ to 4½-inches. (2) Borne: Singly. (3) Form: High centered, flattening upon opening, petals quill and reflex. (4) Petalage: Number of petals under normal conditions — about 30 to 32. (5) Color: As flower opens color remains brick red lightening only slightly from 35A and B to 35C and D until flower ages (after several days) then color darkens to Jasper red 39A while retaining scattered highlights of 35D. Veining which may be seen in fresher flowers but is inconspicuous there, becomes more noticeable in the lighter colored highlights of the old bloom.

C. *Petals.*—(1) Texture: Thick. (2) Appearance: Velvety to satiny. (3) Form: Obovate, petals quill and reflex. (4) Arrangement: Regularly arranged. (5) Petaloids in center: Many. (6) Persistence: Drop off cleanly. (7) Fragrance: Slight. (8) Lasting quality: Very long lasting on plant and as cut flower.

REPRODUCTIVE ORGANS

A. Stamens, filaments and anthers:

(1) *Arrangement.*—Stamens irregularly about pistils.

(2) *Color.*—Yellow with reddish tone.

B. Pollen: Color — yellow.

C. Styles: Uneven, short, bunched.

D. Stigmas: Color — yellow.

E. Hips: None observed.

PLANT

A. Form: Upright, tall, bushy.

B. Growth: Vigorous, free branching.

C. Foliage: Compound 3 to 7 leaflets.

(1) *Size.*—Medium.

(2) *Quantity.*—Abundant.

(3) *Color.*—New foliage: Upper side — near to 146A, 146B and some reddish tones. Under side — 146A. Old foliage: Upper side — 133A, 139B. Under side — 139C.

(4) *Shape.*—Elliptical, cuspidate.

(5) *Texture.*—Upper side is glossy and under side is dull.

(6) *Edge.*—Serrated.

(7) *Serration.*—Simple.

(8) *Leaf stem.*—Color — near to 139B. Under side — 139C.

(9) *Stipules.*—Long.

(10) *Resistance to disease.*—Mildew — good. Rust — good.

D. Wood:

(1) *New wood.*—Color — near 139C. Bark — smooth, shiny.

(2) *Old wood.*—Color — near 139B. Bark — smooth, shiny.

E. Thorns:

(1) *Thorns.*—Quantity (main stalk): many. On laterals from stalk — few. Form — straight. Length — medium. Color — tan to brown. Position — scattered and grouped.

(2) *Prickles.*—Many.

F. Winter hardiness: Good winter hardiness.

I claim:

1. A new and distinct variety of rose plant of the hybrid tea class, substantially as shown and described, characterized particularly by brick red flowers which darken upon aging, borne primarily singly to a stem and are long lasting on the plant and as cut flowers and a vigorous, upright plant.

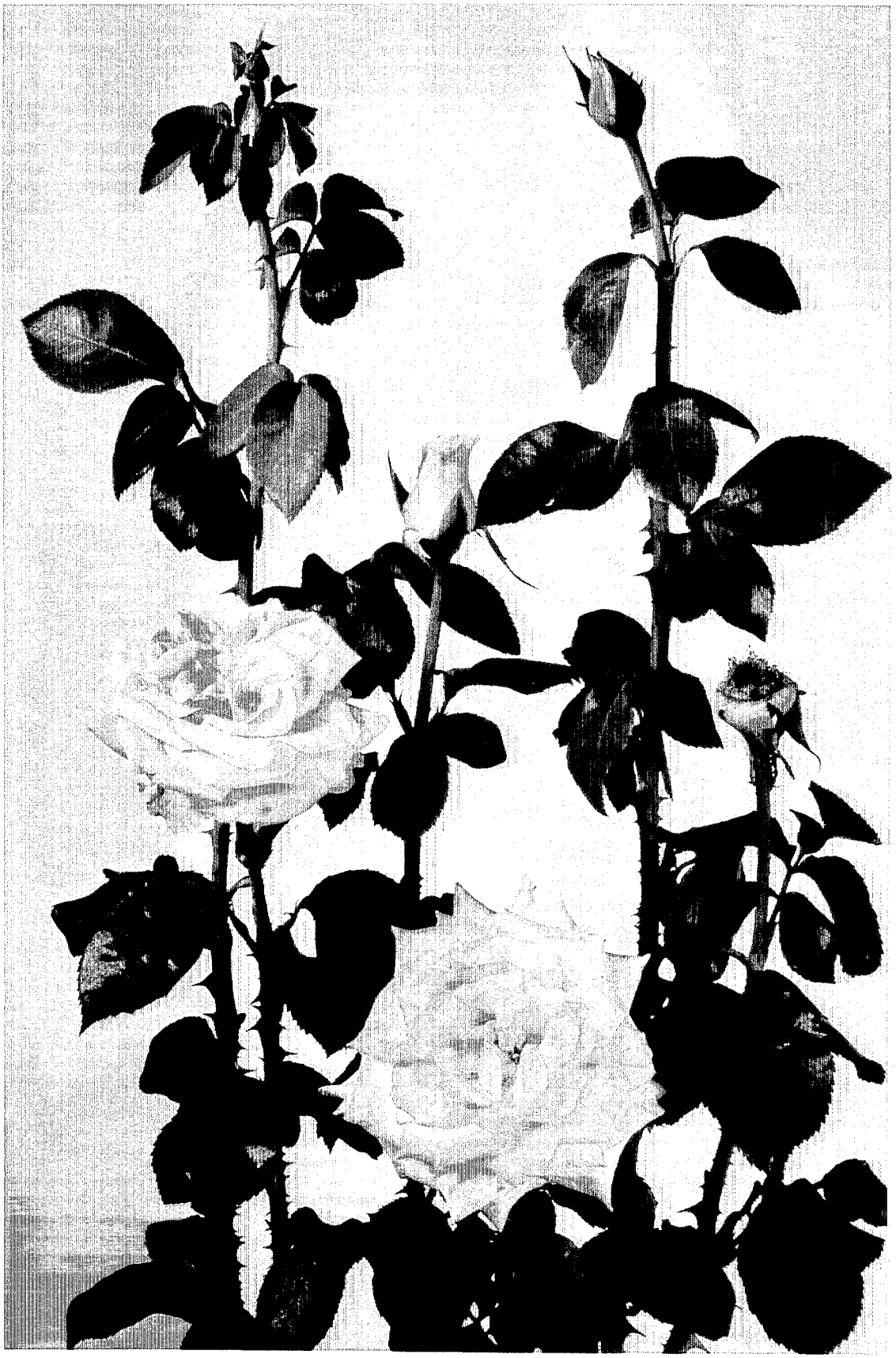

* * * * *